United States Patent
Slone

(10) Patent No.: US 6,280,187 B1
(45) Date of Patent: Aug. 28, 2001

(54) DENTAL HAND TOOL FOR INTERPROXIMAL DENTAL RESTORATIONS

(76) Inventor: Charles E. Slone, 32332 Camino Capistrano Ste. 101, San Juan Capistrano, CA (US) 92675

(*) Notice: Subject to any disclaimer, the term of this patent is extended or adjusted under 35 U.S.C. 154(b) by 0 days.

(21) Appl. No.: 09/502,423

(22) Filed: Feb. 11, 2000

(51) Int. Cl.⁷ ........................................ A61C 3/00
(52) U.S. Cl. ................................. 433/29; 433/141
(58) Field of Search ....................... 433/29, 141, 164, 433/229

(56) References Cited

U.S. PATENT DOCUMENTS

| | | | |
|---|---|---|---|
| 4,130,107 | 12/1978 | Rabl et al. | 126/270 |
| 4,240,692 | 12/1980 | Winston | 350/96.1 |
| 4,365,957 | 12/1982 | Das | 433/144 |
| 4,608,021 | 8/1986 | Barrett | 433/229 |
| 4,666,405 | 5/1987 | Ericson | 433/229 |
| 4,696,646 | 9/1987 | Maitland | 433/149 |
| 4,744,759 | 5/1988 | Bowen | 433/228.1 |
| 4,836,781 | 6/1989 | Meinershagen | 433/141 |
| 5,030,093 | 7/1991 | Mitnick | 433/164 |
| 5,318,446 | 6/1994 | Slone | 433/141 |
| 5,358,404 | 10/1994 | Schumacher | 433/164 |
| 5,634,711 | 6/1997 | Kennedy et al. | 433/29 |
| 5,791,898 | 8/1998 | Maissami | 433/164 |
| 5,797,740 * | 8/1998 | Lundvik | 433/29 |
| 6,186,786 * | 2/2001 | Trushkowsky | 433/29 |
| 6,208,788 * | 3/2001 | Nosov | 433/29 |

* cited by examiner

Primary Examiner—John J. Wilson
(74) Attorney, Agent, or Firm—Gene Scott-Patent Law & Venture Group

(57) ABSTRACT

A light-concentrating dental tool apparatus for use with a visible light curing lamp. The apparatus is comprised of: an elongate handle, including a medially positioned enlarged portion, approximately spherical, providing both distal and mesial end utility elements, the utility elements being made of a light-transparent and light-transmissive material. The distal and mesial end utility elements include a resting and positioning device for the visible light curing lamp, including convex upward facing distal and mesial end surfaces integral with cone-shaped distal and mesial end bodies, preferably hyperbolically-shaped. The end bodies terminate at distal and mesial end workpieces integral with and depending from the end bodies. The distal and mesial end workpieces provide end light disbursing devices for directing a maximum amount of light outwardly therefrom.

13 Claims, 5 Drawing Sheets

DENTAL HAND TOOL FOR INTERPROXIMAL DENTAL RESTORATIONS

BACKGROUND OF THE INVENTION

1. Field of the Invention

This invention relates generally to dental tools for tooth restoration; and, more particularly, to a dental tool for achieving optimum interproximal dental restorations.

2. Description of Related Art

The following art defines the present state of this field:

Rabl et. al. U.S. Pat. No. 4,130,107, describes a device provided for the collection and concentration of radiant energy and including at least one reflective side wall. The wall directs incident radiant energy to the exit aperture thereof or onto the surface of an energy absorber positioned at the exit aperture so that the angle of incidence of radiant energy at the exit aperture or on the surface of the energy absorber is restricted to desired values.

Winston et. al. U.S. Pat. No. 4,240,692 describes a radiant energy transmitting devices operative selectively in concentrative and emissive modes, having transmitting elements including radiant energy transmitting and guiding surfaces at the interface of media of differing indices of refraction for radiant energy. Surfaces generally are of a concavely sloping configuration consistent with reflecting, for example, extremal energy rays entering the element from within a defined field of acceptance at an energy inlet onto an energy trap or, in the alternative, extremal rays from an energy source through an energy outlet within a defined field of emission. The energy source or trap is preferably an energy transducer such as a photoelectric device.

Schumacher et. al. U.S. Pat. No. 5,358,404, describes an apparatus for compressing and adapting filling material introduced into a dental cavity with an elastic punch which is fixed in or on a holder.

Das, et. al. U.S. Pat. No. 4,365,957, describes a periodontal surgical instrument which includes a handle, shank and a cutting head. The cutting head possesses two interior surgical blades each possessing terminus points having their confluence at a substantial V-shape to form an apex. At least one exterior surgical blade is positioned on the cutting head with its beginning at a first point substantially equal to the terminus of one of the adjacent blades. A method of use is also described for this periodontal surgical instrument for Gingivectomy and Gingivoplasty operations.

Meinershagen et. al. U.S. Pat. No. 4,836,781 describes a dental tool for assisting in cavity repair in two adjacent teeth by facilitating removal of matrix bands therefrom after installation of filler restoration material. The tool includes a shank terminating in a bifurcated end portion, each branch of the bifurcated end portion terminating in a working surface having an inner edge. The inner edges of the working surfaces are separated by a gap having a width sufficiently large to accommodate a dental matrix band and sufficiently narrow to enable the working surfaces to maintain tight common interproximal contact with the filler restoration material in adjacent teeth.

Mitnick et. al. U.S. Pat. No. 5,030,093, describes a method and apparatus for placing, compacting and shaping a light-activated dental restorative material in a cavity preparation or between adjacent teeth and for polymerizing said restorative material in said cavity preparation or between said teeth to produce a restorative. A mirror/oral illuminator and a combination mirror and fiber optic probe are also disclosed.

Ericson, et. al. U.S. Pat. No. 4,666,405, describes a method of preparing a class II dental filling of a light-hardening filling material in a drilled-out tooth surrounded by a matrix band, the drilled-out tooth is filled with a light-hardening filling material in which the lower part of a light-transmitting adapter having a recess and attached to a light conductor, is pushed down into a filling material so that light is spread in the deeper parts of the filling, while at the same time the lower part of the adapter is pressed against the point of contact of the adjacent tooth while the filling is hardened so that satisfactory proximal contact is obtained. A lighttransmitting adapter comprises an upper part having a recess for receiving a light conductor and a conical lower part adapted to conduct light-hardening filling material down into a drilled-out tooth. The lower part of the adapter is pressed against a matrix band surrounding the tooth so that satisfactory proximal contact with the adjacent tooth is obtained, while at the same time the deeper parts of the filling are made accessible to light from the light conductor.

Maitland et. al. U.S. Pat. No. 4,696,646 describes a device for use in composite resin dental restoration and a method for overcoming the difficulty of establishing sufficient separation to provide firm and properly located interproximal contact. This invention creates an easy, predictable method for establishing proper interproximal contact pressure and anatomical form. The wedge is used in a method which establishes predictable interproximal static contour relationships with matrix systems, providing the necessary additional interproximal separation and reducing the thickness of the composite resin to be cured by light catalysis to insure more complete curing in the deeper recesses in the cavity preparation.

Barrett et. al. U.S. Pat. No. 4,608,021 describes a method and apparatus for restoration of teeth using light curable restoratives while assuring interproximal contact between the restored tooth and an adjacent tooth. The apparatus is in the form of a triangle-like block defining two arms converging at a common point and which are of a different length. The longer of the two arms is provided with a camming surface on the end thereof opposite from the common pointed edge whereas the shorter of the two arms is provided with an abutment surface on the end thereof opposite from the common pointed edge. A tooth cavitation opening through a vertical tooth surface about which a matrix band has been tightened is filled by alternate deposition and curing of successive layers of the light curable restorative to a level at or below the plane of the maximum circumference of the tooth. The block is placed with the shorter arm against the top of the previously cured filling with the abutment surface against the matrix band so that a ledge of cured restorative may be built about the pointed end of the block. Thereafter, the block is removed and reinserted with the longer leg down and operable as a camming strut pivotable about the previously formed step or ledge against the matrix band to deform it outwardly for subsequent filling and curing of the restorative.

Bowen et. al. U.S. Pat. No. 4,744,759 describes a means to decrease the effects of polymerization shrinkage, increase stiffness, decrease the coefficient of thermal expansion and improve the durability of composite restorations by use of inserts are disclosed. Pieces of an aluminoborosilicate glass are phase-separated by heating to 870.degree. C. for 2 hours producing opaque inserts with silica-rich surfaces. Boiling for 1 hour in aqueous 0.5 N NaOH solution removes the surface layer, and produces a rough-textured surface with increased area. The surface texture plus treatment with an organofunctional silane provides for both micromechanical and chemical bonding with composite resins. Cavities in teeth are partially filled with unhardened composite material, and inserts of appropriate size and shape are pressed into the cavity so that the insert constitutes as much as possible of the finished restoration and its surface. The excess extruded composite material is removed with a hand instrument, and the composite containing the insert is light cured. The glass insert, together with the surrounding hardened composite, is contoured with high-speed rotary diamond instruments. Alternative types of inserts are also described.

Lazarof et. al. U.S. Pat. No. 5,098,292 describes a dental instrument for use in filling cavities in teeth with a light-activated filling compound which includes a condensing tip constructed from a plastic or glass fiber optic material. A source of light, either external to the instrument, or contained therewithin, can be selectively energized to enable controlled activation of the activator in the filling compound as the compound is being packed and shaped within the cavity by the condenser tip of the instrument. The dental instrument includes a suction cup removably connected to the tip for releasably gripping a dental overlay.

Cartwright et. al. U.S. Pat. No. 2,138,726 describes a girdling tool having two handles, each handle terminating at one end with a jaw, said handles being pivotally connected, adapting the jaws to be opened and closed, cutting blades convex in shape, each blade terminating at an approximate point, said blades being arranged on the jaws in pairs, the blades forming each pair being positioned on diverging planes, the greatest divergence between the blades of each pair being at the points of the blades, two pairs of blades being attached to one jaw, the two pairs of blades thereon being arranged so that the sharpened edges of one pair diverge from the sharpened edges of the other pair, the cooperating jaw having one pair of blades thereon, the one pair of blades on said cooperating jaw being positioned so that the sharpened edges thereof are on the same approximate plane as the cooperating blades on the jaw having two pairs of blades thereon.

Maissami et. al. U.S. Pat. No. 5,791,898 describes an improved light-transmitting apparatus and methods for polymerizing light-hardening dental fillings of Class II resins. In the improved apparatus and methods, a magnified prism is constructed in the middle of a light-transmitting apparatus that transforms broad light from a light transmitting source to a concentrated light to the center of the focal point of the tip of the apparatus. The improved apparatus and methods permit the optional connection of the light-transmitting apparatus to a light source.

Slone et. al. U.S. Pat. No. 5,318,446, describes an apparatus and method is provided for preparing a tight proximal contact between a tooth to be filled and an adjacent tooth. A tool head provides a first convex surface extending downwardly to a linear ridge. The head is divided into a pair of side-by-side fingers separated by a channel. The linear ridge defines the tip of each finger. The head is of a size to fit into a prepared cavity in a tooth. The head further provides a stepped surface, in opposition to the first convex surface, that extends downwardly to the linear ridge. Alternately, the head provides a second convex surface, in opposition to the first convex surface, that extends downwardly to the linear ridge. An elongated tool handle has a first and a second opposing bent ends. The first bent end has a 90 degree bend, and the second bent end has a 45 degree bend, such that the single tool may enable the formation of both distal and mesial contacts.

The prior art describes various mechanisms, relating to dental tools for filling cavities and to the efficient collection of light for curing filling materials. Both Winston et. al. U.S. Pat. No. 4,240,692 and Rabl et. al. U.S. Pat. No. 4,130,107, describe devices provided for the collection and concentration or transmission of radiant energy devices using reflective side walls. However, the prior art does not teach a dental tool apparatus with enhanced light-concentrating means and a means for reducing the effect of cured composite shrinkage during tooth restoration which also is enabled to ensure the ideal contact between the restored tooth and an adjacent distal or mesial tooth after restoration. The present invention fulfills these needs and provides further related advantages as described in the following summary.

SUMMARY OF THE INVENTION

The present invention teaches certain benefits in construction and use, which give rise to the objectives described below.

The present invention provides a light-concentrating dental tool apparatus for use with a visible light curing lamp, the apparatus comprised of an elongate handle including a medially positioned enlarged portion, approximately spherical, providing distal and mesial end utility elements, the utility elements being made of a light transparent and light transmissive material, the utility elements including a resting and positioning device for the visible light curing lamp, including convex upward-facing end surfaces integral with cone-shaped end bodies, preferably hyperbolically-shaped, the end bodies terminating at an end workpiece integral with and depending from the end bodies, the end workpiece providing an end light disbursing device for directing light outwardly therefrom.

A primary objective of the present invention is to provide a dental apparatus having advantages not taught by the prior art.

Another objective is to allow a dentist to obtain tight proximal contacts easily and quickly.

A further objective is to provide a dental instrument of the character described which is compact, lightweight, easy to use and inexpensive to manufacture.

A further objective is to provide separate, labeled ends of the instrument for quick identification.

A further objective is to increase the life of the instrument by coating it with a hard layer.

A further objective is to provide for a proper anatomically shaped restoration with convex surfaces ideally positioned.

A further objective is to provide maximum light throughput to the tip of the instrument.

A further objective is to provide an enlarged enhanced gripping surface to allow pressure to be applied at either the distal or mesial end of the instrument through a simple manual push or pull movement.

A further objective is to minimize the effect of shrinkage of the curable composite resin in a proximal box.

A further objective is to enable use of the apparatus in conservative preparations.

A further objective is to allow ideal positioning of the apparatus relative to the occlusal plane.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

Figure 1:
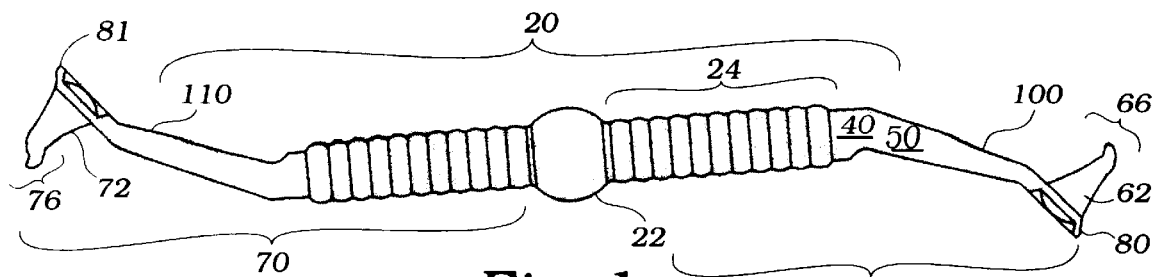
FIG. 1 is a side elevational view of the preferred embodiment of the present invention.
Figure 2:
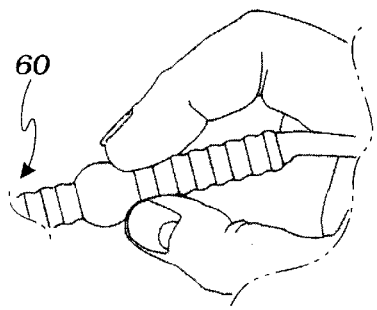
FIG. 2 is a partial view of FIG. 1 showing proper finger positioning while using a distal tip of the invention.
Figure 3:
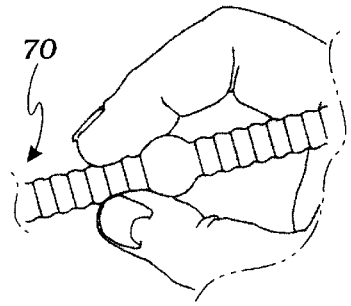
FIG. 3 is similar to FIG. 2 but showing proper finger positioning while using a mesial tip of the invention.
Figure 4:
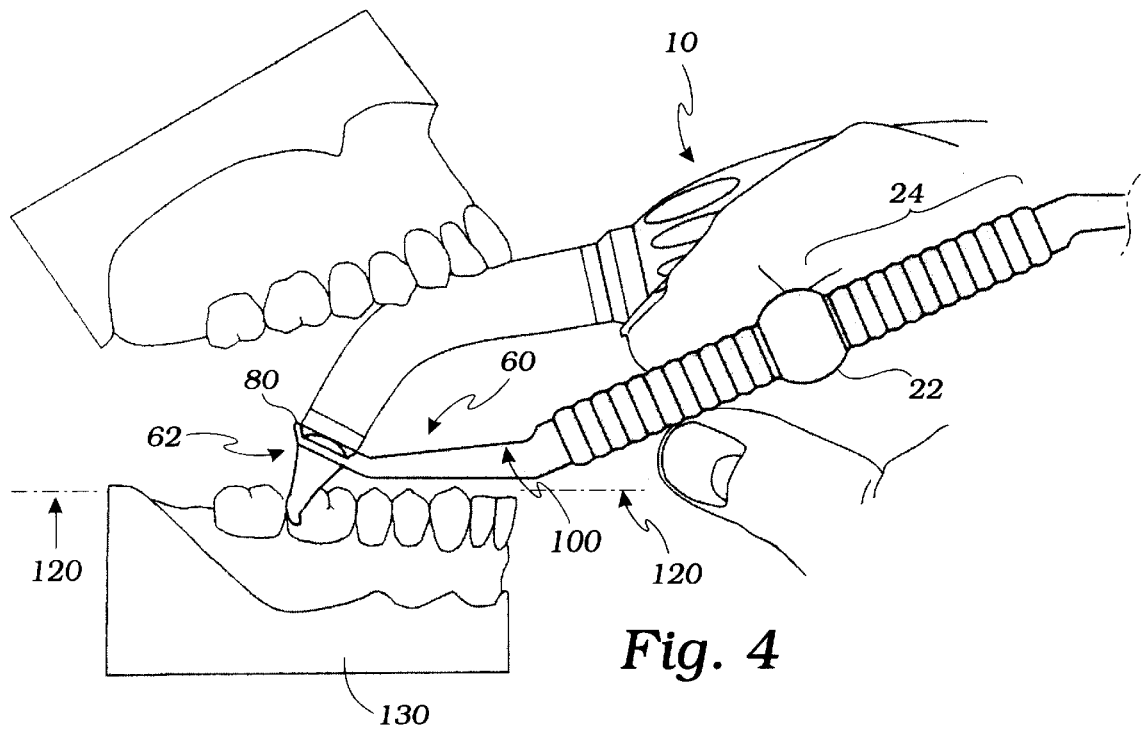
FIG. 4 is an elevational view of the invention in use.
Figure 5:
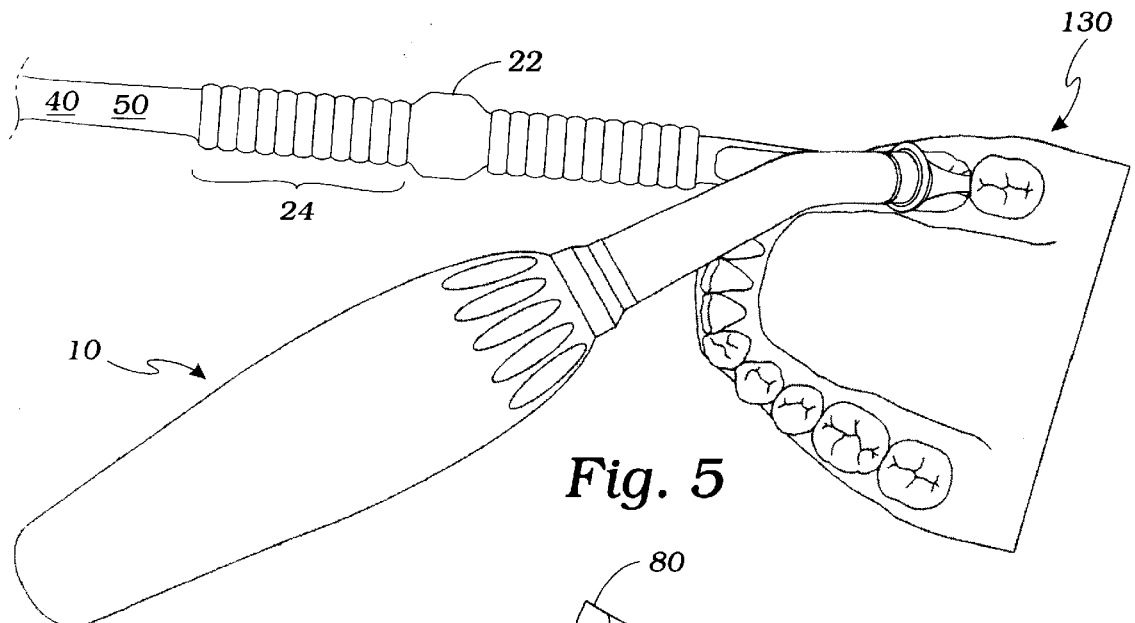
FIG. 5 is a top plan view of the invention in use as shown in FIG. 4.

FIG. 1 illustrates the invention, an apparatus for preparing a tight proximal contact between a tooth to be filled 5 and an adjacent tooth 6. This description of the apparatus incorporates by reference a prior patent by the present applicant, Slone et. al U.S. Pat. No. 5,318,446, which is attached hereto. The present apparatus is a light-concentrating dental hand tool for use with a visible light curing lamp 10, the apparatus comprising an elongate handle 20, approximately four inches in length and weighing no more than two ounces, with an ergonomic design allowing both distal and mesial contacts to be made with equal ease. The handle 20 is manufactured from a light-transparent and light-transmissive material comprised of a steam autoclaveable, optically transparent engineering polymer such as polycarbonate. Inventively, the apparatus'entire outer surface 50 is coated with a proprietary hard amorphous layer 40. This proprietary hard layer 40 preferably has diamond-like properties, including high hardness, optical transparency, high electrical resistance, chemical resistance, elasticity, and a very low coefficient of friction, which increases wear resistance of the outer surface 50.

The handle 20 includes a medially positioned enlarged portion 22, approximately spherical, as shown in FIGS. 1–4, enabled for tactilely positioning the handle 20 in a hand. The medially positioned enlarged portion 22 of the handle 20 inventively provides an enhanced gripping surface having a series of concentric annular grooves 24 for providing a firm grasp of the handle 20 in a hand, thereby improving leverage.

The handle 20 provides, at opposing ends, identical distal and mesial end utility elements 60 and 70 respectively, as shown in FIG. 1. The distal and mesial end utility elements 60 and 70 include corresponding distal and mesial end bodies, 62 and 72, respectively, as shown in FIGS. 6, 7, 12, and 13, also identical. The distal and mesial end bodies 62 and 72 are cone-shaped, each providing an inventively hyperbolic surface of such conformation so as to minimize the loss of light passing through them.

Integral with the distal and mesial end bodies 62 and 72 are convex, preferably spherical, upwardly facing surfaces 64 and 74, also identical, as shown in FIGS. 6, 7, 12, and 13. Both upwardly facing surfaces 64 and 74 have acceptance angles of at least 55 angular degrees, as shown in FIG. 8, through which the light from the visible light curing lamp 10 is directed toward the apertures of the instrument (distal aperture, 65; mesial aperture, 75) at the ends of the distal end workpiece 66 and the mesial end workpiece 76. Light disbursing at the distal and mesial aperture points 65 and 75, respectively, is improved by the convex, preferably spherical shape of the upwardly facing surfaces 64 and 74.

Figure 6:
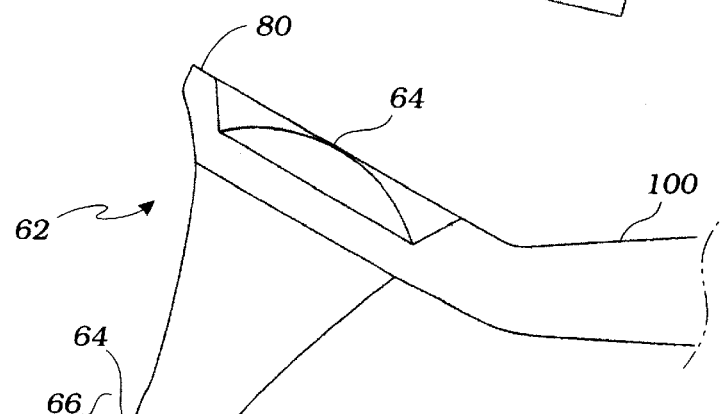
FIG. 6 is an enlarged view of the distal tip showing a penetration depth guide means thereof.

Inventively, the distal end utility element 60 and mesial end utility element 70 include resting and positioning means for the visible light curing lamp 10. The resting and positioning means is comprised of two elements. The first is the upwardly facing surfaces 64 and 74, as shown in FIG. 6. The second element of the resting and positioning means is a distal and mesial annular lip 80 and 81, identical in both the distal and mesial end bodies 62 and 72, angled above and out from the base of the upwardly facing surfaces 64 and 74, which allows an optimum placement of the visible light curing lamp 10 in physical contact with either side of the distal or mesial annular 80 and 81. The distal and mesial annular lip 80 and 81 protrude to a height equal to or above the highest point of the upwardly-facing surfaces 64 and 74 so that the visible light curing lamp 10 rests only on the distal or mesial annular lip 80 and 81 and not on the upwardly facing surfaces 64 and 74.

Figure 7:
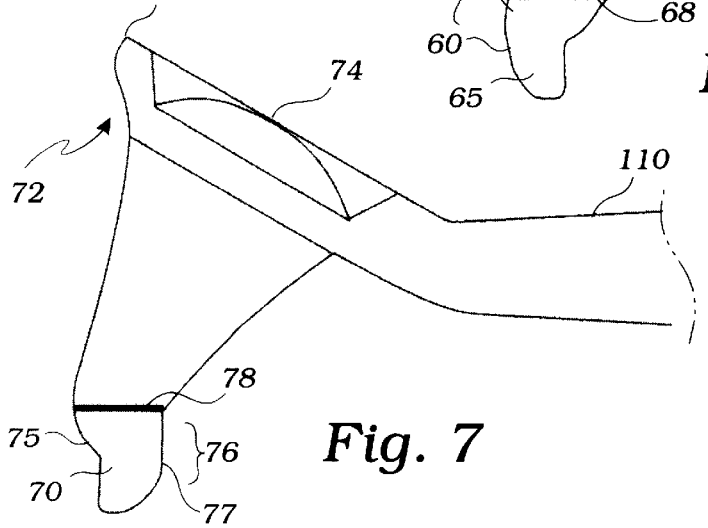
FIG. 7 is an enlarged view of the mesial tip showing a penetration depth guide means thereof.
Figures 8, 9:
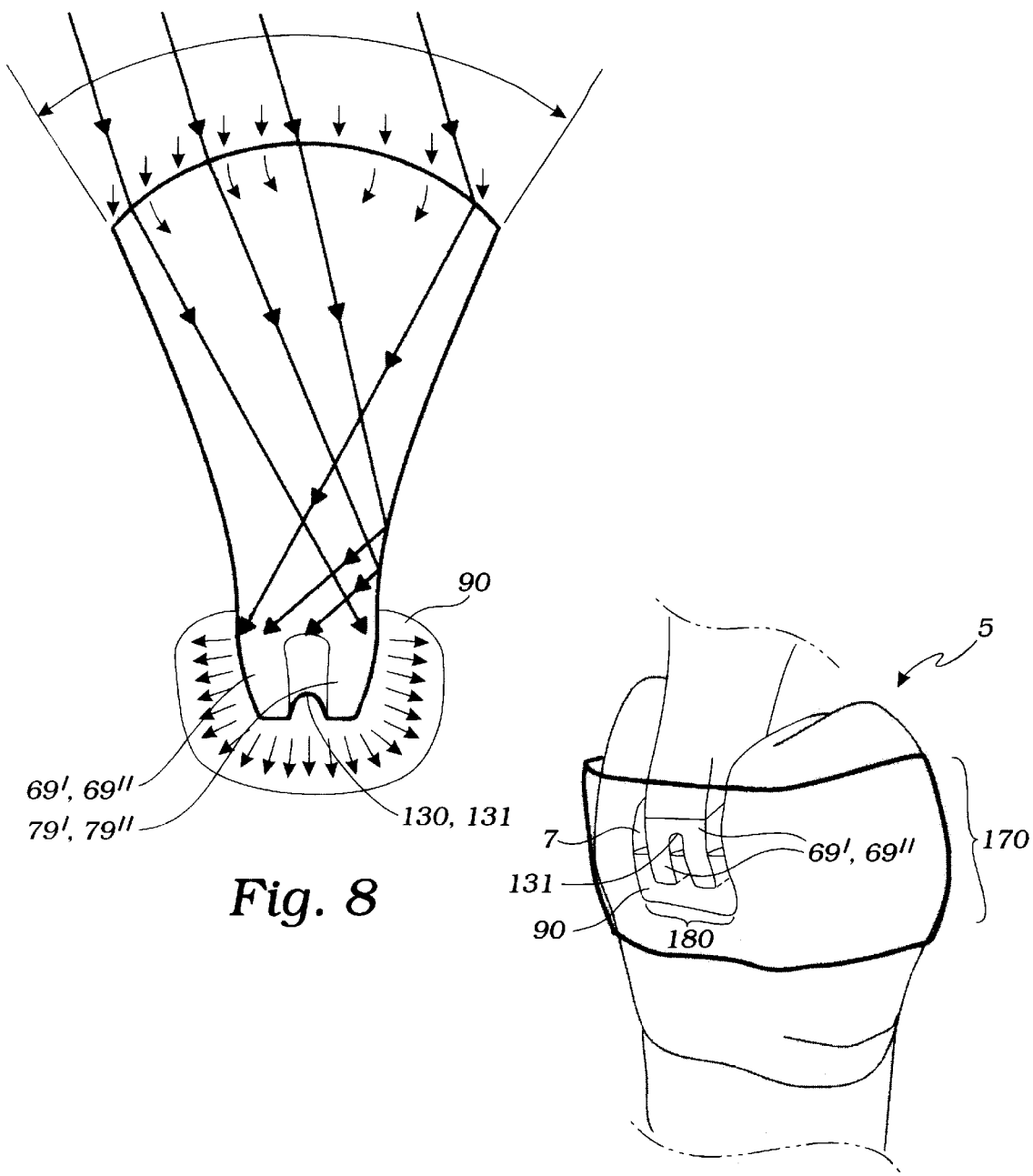
FIG. 8 is a schematic diagram of the invention showing typical light rays transmitted within and into a composite resin adjacent thereto;.
FIG. 9 is a perspective view showing placement of a matrix band on a tooth and placement of a curable composite resin and the invention therein.
Figure 10:
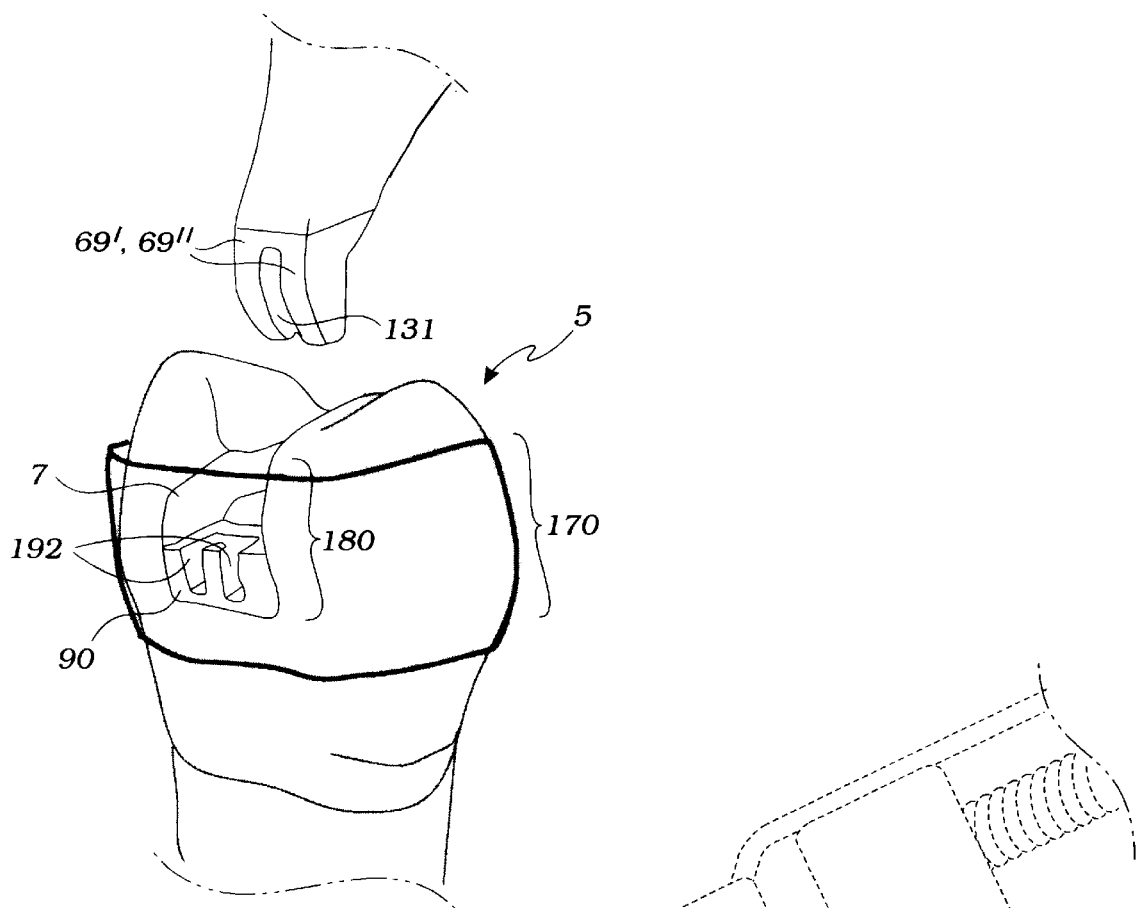
FIG. 10 is similar to FIG. 9 showing the composite resin post cure.
Figure 13:
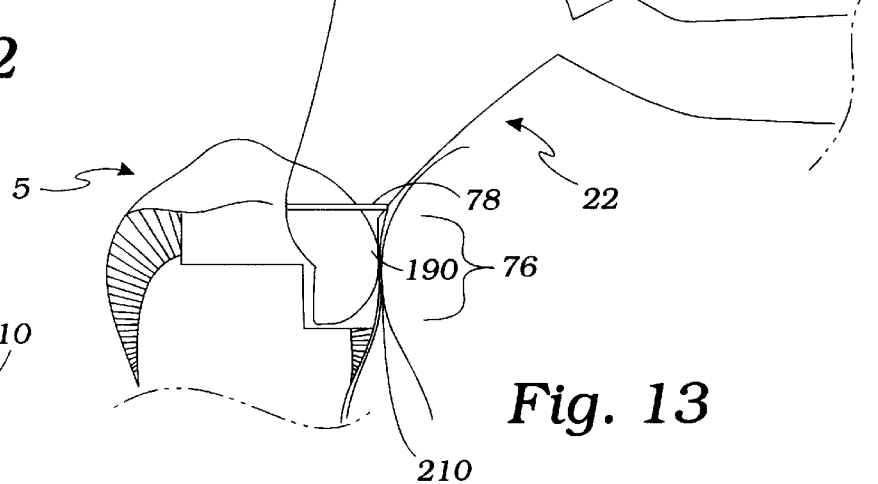
FIG. 13 is an elevational schematic view showing proper placement of the mesial tip.
Figure 14:
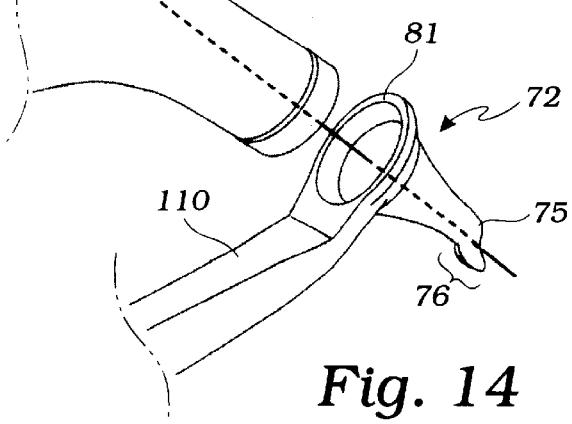
FIG. 14 is a perspective view showing proper alignment of a light source with the mesial tip.

The distal and mesial end bodies 62 and 72 terminate at a corresponding distal end workpiece 66 and mesial end workpiece 76, respectively, as shown in FIG. 1, 6, 7, 12, 13, and 14, integral with and depending from the distal and mesial end bodies 62 and 72. The distal end workpiece 66 and mesial end workpiece 76 disburse light outwardly through the distal and mesial apertures 65 and 75 into the surrounding curable composite resin 90 as shown in FIG. 8 and FIG. 14, thereby enabling faster light curing of the resin 90 used for filling the cavity 7 in a tooth 5. The distal end workpiece 66 and the mesial end workpiece 76 are distinct from each other. Whereas both are rounded and convex on one side; inventively, the convex height contour 67 on the distal end workpiece 66 faces outwardly, away from the dentist as he or she holds the instrument. On the mesial end workpiece 76, the convex height contour 77 faces inwardly, toward the dentist as he or she holds the instrument, as shown in FIGS. 6 and 7. The distal end workpiece 66 and the mesial end workpiece 76 are contoured differently because the dentist applies pushing force to one (distal) and pulling force to the other (mesial).

The distal and mesial end bodies 62 and 72 include identical corresponding distal and mesial depth-of-workpiece penetration guiding means, the distal and mesial marginal ridge guides 68 and 78, as shown in FIG. 6, 7, 13, and 13. Inventively, the guides are circumferentially laser-etched into the base of the distal and mesial end workpieces 66 and 76 and determine the ideal depth at which the distal and mesial end workpieces 66 and 76 are inserted into the resin 90.

Adjacent to the distal end workpiece 66 and the mesial end workpiece 76, the handle 20 provides identical distal and mesial flat surfaces 100 and 110, as shown in FIGS. 6, 7, 12, and 13. The distal and mesial flat surfaces 100 and 110 function to visually align the apparatus with the occlusal plane 120 of a mouth 130. Inventively, the convex upwardly facing distal and mesial surfaces 64 and 74 are set at an angle of between 150 and 160 degrees with respect to the respective adjacent distal and mesial flat surfaces 100 and 110. This angulation scheme allows the distal and mesial light-disbursing apertures 65 and 75, respectively, to be focused into the patient's mouth at an ideal 30 degree angle 220, FIG. 4.

Inventively, the distal end workpiece 66 and the mesial end workpiece 76 are each bifurcated into a pair of side-by-side fingers, identical at both the distal and mesial ends of the instrument—workpiece fingers 69' and 69" (distal) and 79' and 79" (mesial), separated by a hollow channel 131 (distal) and 132 (mesial) that, again, is identical at both the distal and mesial ends of the instrument and runs parallel to the apparatus and is centered between the sides of the each pair of distal and mesial end workpiece fingers 69' and 69" and 79' and 79". This bifurcation of the distal end workpiece 66 and the mesial end workpiece 76 increases the surface area through which light can be disbursed through the distal and mesial apertures 65 and 75 and into the surrounding resin 90. Inventively, the distal and mesial end workpiece fingers 69' and 69" and 79' and 79" are each adapted for providing a surface contact with a dental matrix band 170.

In operation, a proximal box 180 in a tooth to be filled 5 is prepared in a conventional manner as follows: approximately one-half of the volume of the proximal box 180 is filled with a resin 90. The distal end workpiece 66 or mesial end workpiece 76 is placed into the proximal box 180 such that the distal and mesial end workpiece fingers 69' and 69" and 79' and 79" are immersed in the resin 90, as shown in FIGS. 8 and 9. The matrix band 170 is then placed between the tooth 5 to be filled and an adjacent tooth 6 adjacent to the proximal box 180, as shown in FIGS. 9, 10, 11, and 12. The distal and mesial end workpiece fingers 69' and 69" and 79' and 79" push against the adjacent tooth 6 through the matrix band 170, preferably at the junction 190 of the incisal and middle third of the tooth 5. The medially positioned enlarged portion 22 of the handle 20 enhances the pressure that can be applied at either the distal end workpiece 66 or mesial end workpiece 76, therefore enabling the contact to be made with enough force by a simple push for distal contacts or pull for mesial contacts.

Figure 11:
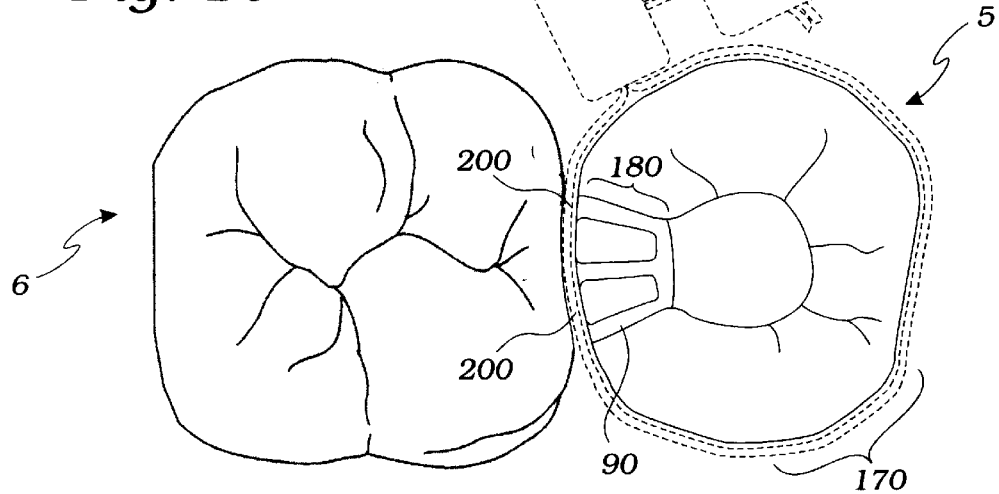
FIG. 11 is a top plan view showing the manner of placement of the matrix band, curable composite resin and placement of the invention therein.
Figure 12:
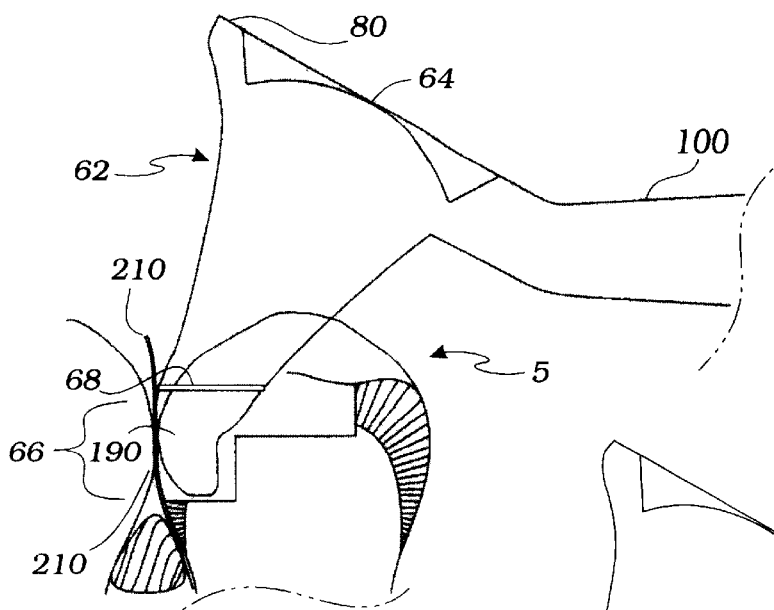
FIG. 12 is an elevational schematic view showing proper placement of the distal tip.

After the curing of the resin 90 that has been placed in the proximal box 180, a hard bridging structure 200 remains between the tooth 5 and the adjacent tooth 6, as shown in FIG. 11. When the matrix band 170 is removed, the adjacent tooth 6 shifts back by approximately the width of the matrix band 170 so that contact between the tooth 5 and the adjacent tooth 6 is attained even after the matrix band 170 no longer separates the tooth 5 and the adjacent tooth 6. The dentist fills the remainder of the volume of the proximal box 180 with the resin 90, including the pronged-shaped hollows 192 left in the resin by the distal and mesial end workpiece fingers 69' and 69" and 79' and 79".

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A light concentrating dental tool apparatus for use with a visible light curing lamp, the apparatus comprising:

an elongate handle providing a distal end utility element, the utility element being made of a light transparent and light transmissive material, the distal end utility element including a resting and positioning means for the visible light curing lamp including a convex upwardly facing distal end surface integral with a modified-cone shaped distal end body, the distal end body terminating at a distal end workpiece integral with and depending from the distal end body, the distal end workpiece adapted for pushing a matrix band into contact with an adjacent tooth, the distal end workpiece further providing a distal end light disbursing means for directing light outwardly therefrom.

2. The apparatus of claim 1 further comprising a mesial end utility element, the mesial end utility element being made of a light transparent and light transmissive material, the mesial end utility element including a mesial end resting and positioning means for the visible light curing lamp including a convex upward facing mesial end surface integral with a modified-cone shaped mesial end body, the mesial end body terminating at an integral mesial end workpiece integral with and depending from the mesial end body, the mesial end workpiece adapted for pulling the matrix band into contact with an adjacent tooth, the mesial end workpiece further providing a mesial end light disbursing means for directing light outwardly therefrom.

3. The apparatus of claim 2 wherein the elongate handle includes a medially positioned enlarged portion enabled for improved leverage in applying pushing and pulling forces thereon.

4. The apparatus of claim 2 wherein the medially positioned enlarged portion is approximately spherical.

5. The apparatus of claim 2 wherein the elongate handle provides an enhanced gripping surface having a series of concentric annular grooves for providing a firm grasp of the elongate handle in a hand.

6. The apparatus of claim 2 further comprising an autoclaveable hard coating applied to an outer surface of the apparatus, the coating enabled for increasing wear resistance of the outer surface.

7. The apparatus of claim 2 wherein the elongate handle provides a distal end flat surface adjacent to the distal end workpiece and a mesial end flat surface adjacent to the mesial end workpiece, said flat surfaces functional for aligning the apparatus with the occlusal plane of a mouth.

8. The apparatus of claim 2 wherein the convex upward facing surfaces at the distal and mesial ends of the apparatus are set at between 145 and 155 angular degrees with respect to the respective adjacent said flat surfaces so as to enable use of the apparatus in the mouths of both adults and children.

9. The apparatus of claim 2 wherein the convex upward facing mesial and distal end surfaces are spherical for enabling improved light concentration.

10. The apparatus of claim 2 wherein the distal end and the mesial end light disbursing means are each adapted for providing a surface contact with the dental matrix band.

11. The apparatus of claim 2 wherein the mesial and distal modified-cone shaped end bodies each provide a hyperbolic surface of such conformation as to minimize the loss of light passing through the modified-cone shaped end bodies.

12. The apparatus of claim 2 further comprising a depth of workpiece penetration guiding means.

13. The apparatus of claim 2 wherein the mesial end and the distal end workpieces are each bifurcated for improved light transmission from said workpieces.

\* \* \* \* \*